(12) United States Patent
Naya (10) Patent No.: US 8,113,843 B2
(45) Date of Patent: Feb. 14, 2012

(54) APPARATUS FOR ANALYZING OPERATIONS AND METHOD FOR ANALYZING OPERATIONS

(75) Inventor: Futoshi Naya, Nara (JP)

(73) Assignee: Empire Technology Development LLC, Wilmington, DE (US)

( * ) Notice: Subject to any disclaimer, the term of this patent is extended or adjusted under 35 U.S.C. 154(b) by 5 days.

(21) Appl. No.: 12/642,265

(22) Filed: Dec. 18, 2009

(65) Prior Publication Data

US 2011/0140929 A1   Jun. 16, 2011

(30) Foreign Application Priority Data

Dec. 14, 2009   (JP) .................................. 2009-282772

(51) Int. Cl.
*G09B 19/00* (2006.01)

(52) U.S. Cl. ...................................... 434/257

(58) Field of Classification Search .................... 434/65, 434/220, 248–261; 340/573.1, 669–661, 340/5.1; 702/151–153, 182, 189, 19, 94, 702/96, 139–145; 715/705
See application file for complete search history.

(56) References Cited

U.S. PATENT DOCUMENTS

| 5,826,578 A | * | 10/1998 | Curchod ........................ 600/595 |
| 2007/0135225 A1 | * | 6/2007 | Nieminen et al. ............ 473/212 |

FOREIGN PATENT DOCUMENTS

| JP | 63-139574 | 6/1988 |
| JP | 03-026281 | 2/1991 |
| JP | 08-182786 | 7/1996 |
| JP | 10-274918 | 10/1998 |
| JP | 11-308527 | 11/1999 |
| JP | 2002-248188 | 9/2002 |
| JP | 2004-164563 | 6/2004 |
| JP | 2004-283607 | 10/2004 |
| JP | 2005-11178 | * 4/2005 |
| JP | 2005-111178 | 4/2005 |
| JP | 2007-334479 | 12/2007 |
| JP | 2009-282442 | 12/2009 |
| JP | 2010-079443 | 4/2010 |

OTHER PUBLICATIONS

Office Action for Japanese Application No. 2009-282772 mailed May 31, 2010 (with English translation).
Tomine et al., "Construction of Japanese Sign Language Communication System using TVML," Human Communication Group Symposium 2009, The Institute of Electronics, Information and Communication Engineers, Dec. 2009, pp. 1-5 (with English abstract).
Bao, L. et al., "Activity Recognition from User-Annotated Acceleration Data," *Second International Conference on Pervasive Computing*, 2004, pp. 1-17.
Ihara, M. et al., "A gesture collaboration system in networked mixed reality environment," *Technical Report of IEICE*, vol. 99, No. 363, Oct. 10, 1999, pp. 21-26 (with English translation).
Office Action for JP 2009-282772 mailed Feb. 5, 2010 (with English translation).

* cited by examiner

*Primary Examiner* — Timothy Edwards, Jr.
*Assistant Examiner* — Jerold Murphy
(74) *Attorney, Agent, or Firm* — Foley & Lardner LLP (57) ABSTRACT

An operations analysis apparatus for motion includes a prescribed-motion data acquisition unit configured to acquire prescribed-motion data which is measured when an exemplar and an examinee perform a prescribed motion, respectively, and a feature extraction unit configured to extract exemplar features and examinee features, and a transformation matrix calculation unit configured to calculate a transformation matrix between the exemplar features and the examinee features, and a specified-motion data acquisition unit configured to acquire specified-motion data which is measured when the exemplar performs a series of specified motions, and a creation unit configured to, from the acquired set of specified-motion data regarding the exemplar, create a piece of exemplary specified-motion information for the examinee by using the calculated transformation matrix, and a indication unit configured to indicate the piece of exemplary specified-motion information for the examinee.

7 Claims, 6 Drawing Sheets

APPARATUS FOR ANALYZING OPERATIONS AND METHOD FOR ANALYZING OPERATIONS

CROSS REFERENCE TO RELATED APPLICATION

This application claims the benefit of Japanese Application No. 2009-282772 filed on Dec. 14, 2009 which is incorporated herein by reference.

BACKGROUND

1. Technical Field

The present disclosure relates to an apparatus for analyzing operations and method for analyzing operations.

2. Related Art

In general, motion analysis methods, in each of which motions of a human body are measured and analyzed by attaching motion measurement devices to the human body, such as acceleration sensors or gyro sensors, are well known to those skilled in the art (for example, refer to non-patent document 1 below).

Non-Patent document 1: Ling Bao, Stephen S. Intille, "Activity Recognition from User-Annotated Acceleration Data", In Second International Conference on Pervasive Computing, pp. 1-17, 2004

SUMMARY

It is considered that the measurement of motions of the body of a human being, which include specialized motions, such as those of dancing and those of violoncello playing, in addition to general motions, such as those of walking and those of meal taking, and the quantification of a set of data resulting from the measurement enable realization of figuring out differences between motions of two different human beings (for example, differences between motions of an exemplar and motions of a beginner) from analysis of a set of quantified data.

However, even if the exemplar and the beginner perform the same motions, differences therebetween, such as differences in physiques therebetween due to gender, age and the like, differences in individual features therebetween due to a dominant hand, a dominant foot and the like, discrepancies between the positions of sensor devices, which are attached to the exemplar and the beginner, respectively, cause two sets of data resulting from measurement of the same motions performed by the exemplar and the beginner to be different from each other.

Accordingly, for example, even if a piece of data regarding certain motions performed by the exemplar is indicated to the beginner for advice thereto, a situation, in which the indicated piece of motion data is not always most appropriate for the beginner, is likely to occur.

Accordingly, it is desirable to provide a new motion analysis device and a new motion analysis method which enable realization of eliminating differences in motion data due to the above-described differences, such as those in physiques.

An operations analysis apparatus for motion includes a prescribed-motion data acquisition unit configured to, in the case an exemplar and an examinee perform a series of prescribed motions, acquire sets of prescribed-motion data regarding the exemplar and the examinee, respectively, a feature extraction unit configured to, from the acquired sets of prescribed-motion data, extract features of the set of prescribed-motion data regarding the exemplar and features of the set of prescribed-motion data regarding the examinee, a transformation matrix calculation unit configured to calculate a transformation matrix for performing a transformation between the features of the set of prescribed-motion data regarding the exemplar and the features of the set of prescribed-motion data regarding the examinee, a specified-motion data acquisition unit configured to, in the case where the exemplar performs a series of specified motions, acquire a set of specified-motion data regarding the exemplar, a creation unit configured to, from the acquired set of specified-motion data regarding the exemplar, create a piece of exemplary specified-motion information for the examinee by using the calculated transformation matrix, and an indication unit configured to indicate the created piece of exemplary specified-motion information for the examinee.

Preferably, in the operations analysis apparatus for motion, the specified-motion data acquisition unit is further configured to acquire a set of specified-motion data in the case where the examinee performs the series of specified motions, and the indication unit is further configured to indicate a piece of examinee specified-motion information, which is created on the basis of the acquired set of specified-motion data for the examinee, and the piece of exemplary specified-motion information for the examinee so as to be associated with each other.

Preferably, in the operations analysis apparatus for motion, the prescribed-motion data acquisition unit is further configured to acquire a set of prescribed-motion data measured by at least one motion measurement device which is attached to at least one part of the body of the exemplar, and a set of prescribed-motion data measured by at least one motion measurement device which is attached to on the body of the examinee further, the feature extraction unit is further configured to extract the features regarding the at least one part of the body of the exemplar and the features regarding the at least one part of the body of the examinee, and the transformation matrix calculation unit is further configured to calculate a transformation matrix for performing a transformation between the features regarding the at least one part of the body of the exemplar and the features regarding the at least a one part of the body of the examinee.

Preferably, in the operations analysis apparatus for motion further includes a corresponding interval extraction unit configured to extract the corresponding intervals between the intervals of the set of prescribed-motion data measured by at least one motion measurement device which is attached to the at least one part of the body of the exemplar and the intervals of the set of prescribed-motion data measured by at least one motion measurement device which is attached to the at least one part of the body of the examinee, and the transformation matrix calculation unit is configured to, on the basis of a piece of information regarding the corresponding intervals extracted thereby, calculate a transformation matrix for performing a transformation between the features regarding the at least one part of the body of the exemplar and the features regarding the at least one part of the body of the examinee.

Preferably, the operations analysis apparatus for motion further includes a data transformation unit configured to, in the case where the exemplar is a right-handed person and the examinee is a left-handed person, or the exemplar is a left-handed person and the examinee is a right-handed person, perform a data transformation so that the set of prescribed-motion data regarding the at least one of a dominant hand and a dominant foot of the exemplar corresponds to the set of prescribed-motion data regarding the at least one of a dominant hand and a dominant foot of the examinee.

Preferably, in the operations analysis apparatus for motion, each of the exemplar features and the examinee features include at least one of an acceleration component and an angular-velocity component.

A motion analysis method, the method includes: acquiring sets of prescribed-motion data regarding an exemplar and an examinee, respectively, in the case the exemplar and the examinee perform a series of prescribed motions; extracting features of the set of prescribed-motion data regarding the exemplar and features of the set of prescribed-motion data regarding the examinee from the acquired sets of prescribed-motion data; calculating a transformation matrix for performing a transformation between the features of the set of prescribed-motion data regarding the exemplar and the features of the set of prescribed-motion data regarding the examinee; acquiring a set of specified-motion data regarding the exemplar in the case where the exemplar performs a series of specified motion; creating a piece of exemplary specified-motion information for the examinee from the acquired set of specified-motion data regarding the exemplar by using the calculated transformation matrix; and demonstrating the created piece of exemplary specified-motion information for the examinee.

BRIEF DESCRIPTION OF THE DRAWINGS

FIG. 2 is a diagram illustrating an example in which motion measurement devices according to an embodiment of the present disclosure are attached to the body of an examinee and the like;

DESCRIPTION OF THE PREFERRED EMBODIMENTS

Hereinafter, preferred embodiments of the present disclosure will be described with reference to drawings.

Figure 1:
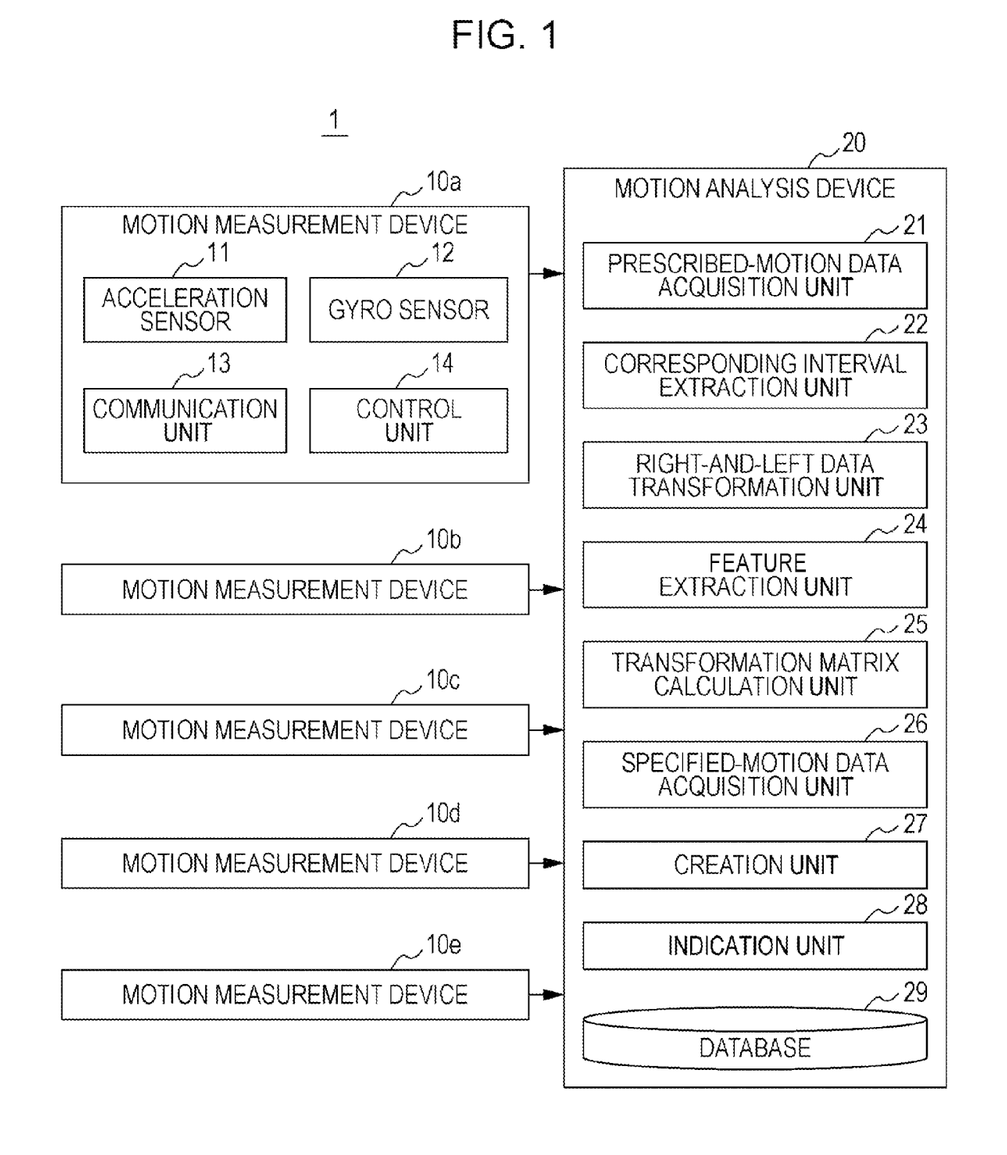
FIG. 1 is a diagram illustrating an outline of a configuration of a motion analysis system according to an embodiment of the present disclosure.

FIG. 1 is a diagram illustrating an outline of a configuration of a motion analysis system 1 according to an embodiment of the present disclosure.

As shown in FIG. 1, the motion analysis system 1 is configured to include motion measurement devices 10a to 10e and a motion analysis device 20, which are connected to one another via a communication link, such as a wireless link or a wired link, and are capable of transmitting and receiving data mutually through the communication link. In addition, the way of transmitting and receiving data to/from the motion measurement devices 10a to 10e and the motion analysis device 20 is not limited to the way via the communication link. For example, a way of transmitting and receiving data via portable media, such as a USB memory, is acceptable.

Figure 2:
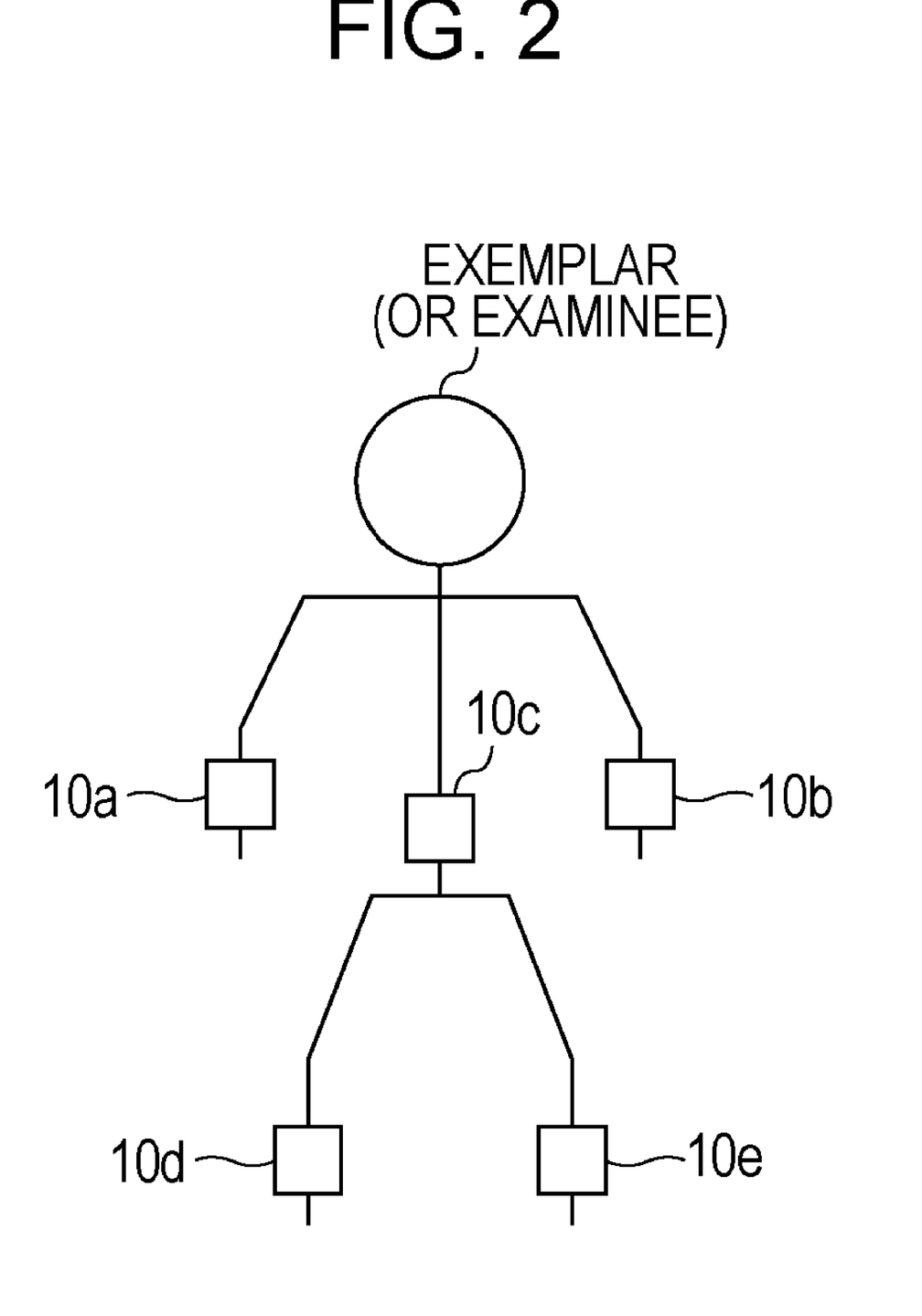

The motion measurement devices 10a to 10e are devices which are attached to the human body of an exemplar A, such as an expert, as well as the human body of an examinee B, such as a beginner, and are configured to each include an acceleration sensor 11, a gyro sensor 12, a communication unit 13 configured to transmit a set of data (prescribed-motion data), which are measured by the acceleration sensor 11 and the gyro sensor 12, to the motion analysis device 20, and a control unit 14 configured to perform control of the communication unit 13, the acceleration sensor 11 and the gyro sensor 12. Each of the plurality of motion measurement devices 10a to 10e is attached to a part of the human body of an exemplar, as well as a part of the human body of an examinee, that is, for example, as shown in FIG. 2, the motion measurement devices 10a, 10b, 10c, 10d and 10e are attached to a right wrist, a left wrist, a waist, a right foot and a left foot, respectively. In addition, FIG. 2 shows an example of a case where the number of the parts to which motion measurement devices are attached is five; however, the number of the parts to which motion measurement devices are attached is not limited to the number in this case, but can be at least more than or equal to one.

In each of the motion measurement devices 10a to 10e according to this embodiment, the acceleration sensor 11 is a triaxial acceleration sensor, which is configured to measure acceleration components in the directions of three dimensional axes (i.e., in an x-axis direction, a y-axis direction and a z-axis direction), and the gyro sensor 12 is a triaxial gyro sensor, which is configured to measure angular-velocity components around three dimensional axes (i.e., around an x-axis, a y-axis and a z-axis).

In addition, the configurations and functions of each of the motion measurement devices 10a to 10e and those of the acceleration sensor 11 and the gyro sensor 12 which are used in each of the motion measurement devices 10a to 10e are fundamentally the same as or similar to those of general motion measurement devices and those of general acceleration sensors and gyro sensors, and thus, are herein omitted from detailed descriptions. Further, the acceleration sensor 11 is not necessary to be the triaxial acceleration sensor described above, but can be a one-axis acceleration sensor or a biaxial acceleration sensor as a substitute therefor. This substitution regarding the acceleration sensor 11 can be similarly applied to a substitution regarding the gyro sensor 12.

The motion analysis device 20 is a device which is configured to acquire sets of motion data transmitted from the motion measurement devices 10a to 10e, which are attached to human bodies of the exemplar A, as well as human bodies of the examinee B, perform a transformation and the like regarding the acquired a set of motion data, and indicate a piece of information resulting from the transformation to the examinee B and the like.

Figure 3:
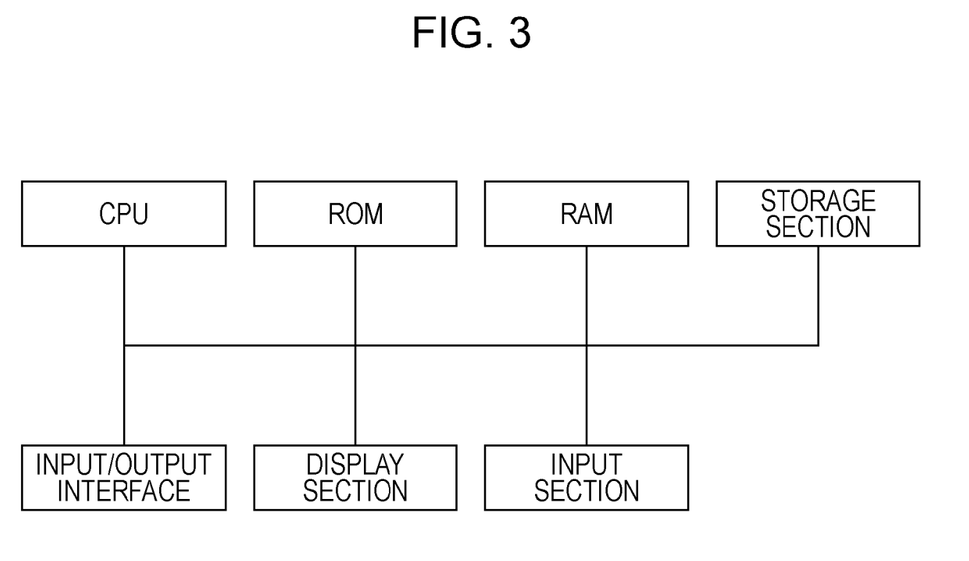
FIG. 3 is a schematic diagram illustrating a configuration of hardware of a motion analysis device according to an embodiment of the present disclosure.

The motion analysis device 20 is configured to, as shown in FIG. 3, include a CPU, and hardware components connected to the CPU via a bus, such ROM modules, RAM modules, a storage unit, a display unit and an input/output interface, which are the same as or similar to those of general computer devices. These hardware components included in the motion analysis device 20 can be those of either a dedicated system or a general-purpose information processing device. For example, the motion analysis device 20 can be constructed by running software which implements motion analysis method according to the present disclosure in a general information processing device.

As shown in FIG. 1, the motion analysis device 20 is configured to include a prescribed-motion data acquisition unit 21, a corresponding interval extraction unit 22, a rightand-left data transformation unit 23, a feature unit 24, a transformation matrix calculation unit 25, a specified-motion data acquisition unit 26, a creation unit 27, a indication unit 28 and a database 29. Each of these units can be realized by, for example, mainly causing the CPU to execute programs stored in the ROM modules and the RAM modules and controlling of each of the hardware components. Further, the database 29 can be realized by using the RAM modules and the storage unit.

As described below, the database 29 is configured to store therein a set of data, each resulting from labeling of a piece of identification information regarding a motion (i.e., a motion label), on each of a set of prescribed-motion data Aa to Ae, which are measured by the motion measurement devices 10*a* to 10*e* attached to the human body of the exemplar A, respectively. Further, in the same manner as or a manner similar to that of the above-described case for the exemplar A, the database 29 is also configured to store therein a set of prescribed-motion data Ba to Be regarding the examinee B.

The prescribed-motion data acquisition unit 21 is configured to store two kinds of sets of prescribed-motion data, one being a set of prescribed-motion data collected in the case where the exemplar A performs prescribed motions, the other one being a set of prescribed-motion data collected in the case where the examinee B performs the prescribed motions. That is, the prescribed-motion data acquisition unit 21 is configured to receive and acquire sets of prescribed-motion data Aa to Ae from the corresponding motion measurement devices 10*a* to 10*e*, which are attached to individual parts of the human body of the exemplar A. Further, in the same manner as or a manner similar to that of the case for the exemplar A, in the case of the examinee B, the prescribed-motion data acquisition unit 21 is configured to receive and acquire sets of prescribed-motion data Ba to Be from the corresponding motion measurement devices 10*a* to 10*e*. Each set of the prescribed-motion data Aa to Ae and Ba to Be can be represented as a time series of data, which is a six dimensional vector v, including acceleration components in the direction of three dimensional axes, i.e., $g_x$, $g_y$ and $g_z$, and angular-velocity components around three dimensional axes, i.e., $a_x$, $a_y$ and $a_z$, and being represented by a formula: $v=(g_x, g_y, g_z, a_x, a_y, a_z)$.

Here, the prescribed motions include a series of prescribed postures/motions which are performed by the exemplar A and the examinee B wearing the motion measurement devices 10*a* to 10*e*. For example, the prescribed motions are a series of prescribed postures/motions regarding a so-called "deep breath", in which, subsequent to the posture of "attention", by stretching arms forward, the posture of "falling in line" is made, further, by raising the arms upward maintaining the condition of stretching the arms, the posture of "raising arms upward so as to point fingertips toward the sky" is made, further, by bringing down the arms in parallel with the front body of the exemplar A or the examinee B, the posture of "stretching the right and left arms in the right-hand and left-hand directions, respectively" is made, and by bringing down arms in parallel with the front body of the exemplar A or the examinee B, the posture of "attention" is made again. Further, in order to allow the series of postures/motions to have stationary conditions each being kept for a certain period of time, for example, in the case of sets of data measured by the acceleration sensors, the series of postures/motions is configured so as to include certain postures, each allowing the values of gravity acceleration components measured at individual parts, to which the motion measurement devices are attached, to be equal to "0", or a maximum value or a minimum value (i.e., +1G or −1G). As a result, it is possible to segment the series of postures/motions into two kinds of conditions, one being stationary conditions in individual postures, the other one being moving conditions from certain postures to postures subsequent thereto, and define each of the stationary conditions and the moving conditions as an interval (a detection interval). For example, in the above-described example, which is the series of postures/motions regarding "a deep breath", it is possible to segment the series of postures/motions into nine prescribed postures/motions, such as the posture of "attention"; the motion from the posture of "attention" to the posture of "falling in line"; the posture of "falling in line"; the motion from the posture of "falling in line" to the posture of "raising arms upward so as to point fingertips toward the sky"; the posture of "raising arms upward so as point fingertips toward the sky"; the motion from the posture of "raising arms upward so as point fingertips toward the sky" to the posture of "stretching the right and left arms in the right-hand and left-hand directions, respectively"; the posture of "stretching the right and left arms in the right-hand and left-hand directions, respectively; the motion from the posture of "stretching the right and left arms in the right-hand and left-hand directions, respectively" to the posture of "attention"; and the posture of "attention".

In addition, besides the above-described series of postures/motions regarding "a deep breath", the prescribed motions can be configured to be a series of prescribed postures/motions resulting from combination of postures/motions using the whole of an upper body, those using the whole of a lower body, and those using an entire body. Furthermore, the prescribed motions can be configured to be a series of postures/motions including characteristic prescribed postures/motions using a dominant hand or a dominant foot of the exemplar A and the examinee B, such as postures/motions related to throwing a ball with his or her right hand, those related to using a kitchen knife with his or her right hand, and those related to kicking a ball with his or her left foot.

The prescribed-motion data acquisition unit 21 is configured to perform labeling of a piece of identification information regarding a motion (i.e., a motion label) on each of the sets of prescribed-motion data Aa to Ae, which is measured by the corresponding motion measurement device among the motion measurement devices 10*a* to 10*e* attached to the human body of the exemplar person A, and includes streams of time series data, each being represented by a six dimensional vector, and corresponding to one of intervals resulting from segmentation of the above-described prescribed motions, and further, store the resultant sets of data in the database 29.

The corresponding interval extraction unit 22 is configured to, by using the sets of prescribed-motion data Aa to Ae regarding the exemplar A and the sets of prescribed-motion data Ba to Be regarding the examinee B, extract the corresponding intervals between intervals of the set of prescribed-motion data regarding the exemplar A and intervals of the set of prescribed-motion data regarding the examinee B by utilizing a method of detecting the degree of similarity between two streams of time series data, such as the DP matching method. That is, by using the DP matching method, intervals/motion labels of the set of prescribed-motion data regarding the examinee B, which correspond to intervals/motion labels resulting from the above-described segmentation of the set of prescribed-motion data regarding the exemplar A are estimated. For example, in the case where intervals, for each of which a piece of motion data measured by the motion measurement device 10*a* attached to the right wrist of the exemplar A corresponds to a piece of motion data measured by the motion measurement device 10*a* attached to the right wrist of the examinee B, are extracted, a piece of motion data during an interval when the posture of "attention" is made by the exemplar A and a piece of motion data during the corresponding interval when the posture of "attention" is made by the examinee B are extracted. In addition, the above-described method using the DP matching method can employ a method similar to existing DP methods, and thus, is herein omitted from detailed descriptions. In this method similar to the existing DP methods, with respect to a distance scale in the DP matching method, for example, a Euclidean distance between pieces of raw data is used.

Figure 4:
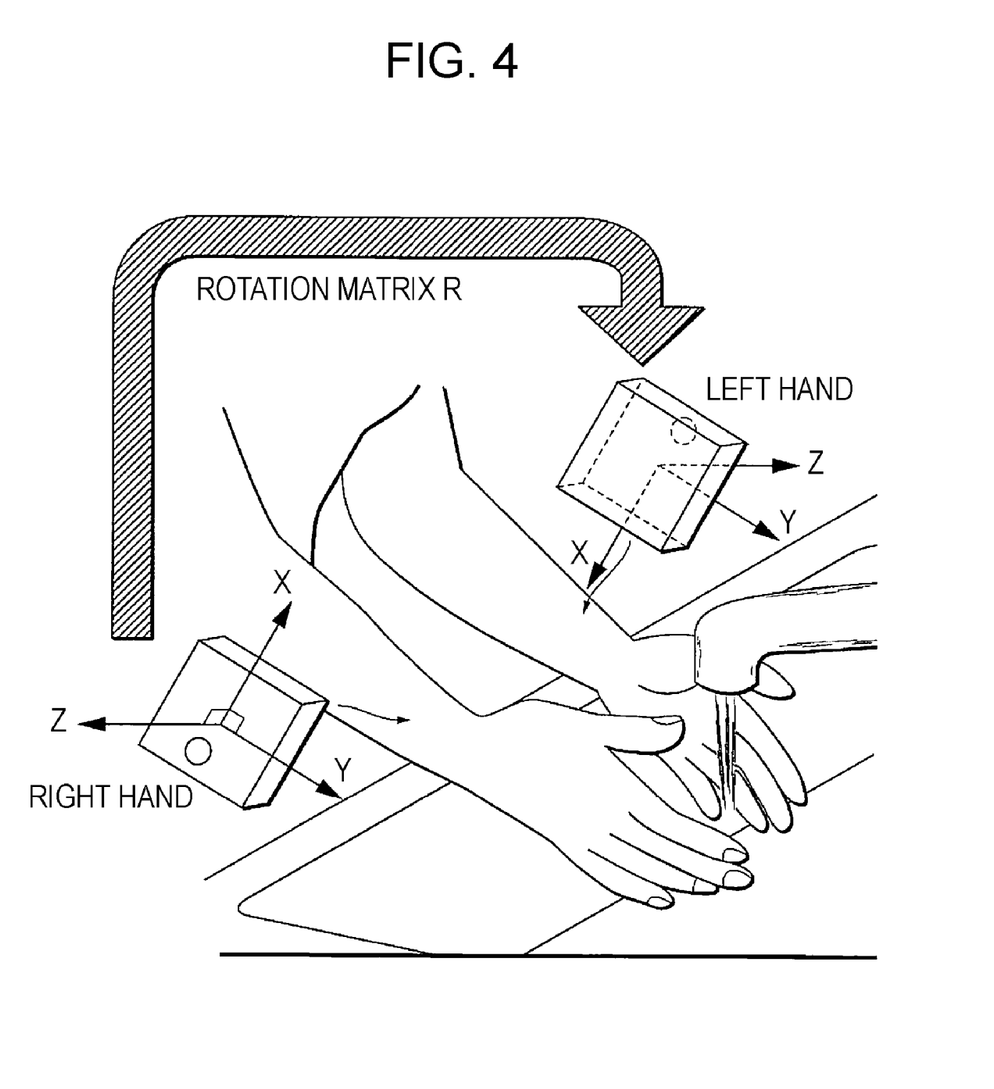
FIG. 4 is a diagram illustrating a rotation matrix for transforming data regarding a right hand into data regarding a left hand, according to an embodiment of the present disclosure.

The right-and-left data transformation unit (a data transformation unit) 23 is configured to, in the case where at least any of a difference between a dominant hand of the exemplar A and a dominant hand of the examinee B and a difference between a dominant foot of the exemplar A and a dominant foot of the examinee B arises, perform a data transformation so as to cause respective sets of prescribed-motion data regarding the corresponding parts (hands and/or foots) of the exemplar person A and the examinee B to correspond to each other. For example, assuming that a piece of information regarding dominant hands and dominant foots of the exemplar A and the examinee B is input to the motion analysis device 20 in advance, in the case where the exemplar A is a right-handed person and the examinee B is a left-handed person, a set of prescribed-motion data regarding the right wrist of the exemplar A (a set of right-hand data), which is measured by the motion measurement device 10a attached to the right wrist of the exemplar A, is transformed into a set of prescribed-motion data regarding the left wrist of the exemplar A (a set of left-hand data). In addition, in the same as or a manner similar to that of the above-described case, sets of prescribed-motion data regarding a non-dominant hand and a non-dominant foot can be transformed. This transformation can be realized, for example, as shown in FIG. 4, by a method of a simple rotating matrix R, which is adopted taking into account the symmetric property of a human body. That is, in the case where the measurement is executed by using a coordinate system shown in FIG. 4, transforming a set of prescribed-motion data resulting from measurement of the right hand into a set of prescribed-motion data as a substitute for a set of prescribed motion data resulting from measurement of the left hand can be achieved by using the following formula (1) so that, with respect to acceleration components, only a component, i.e., a piece of acceleration data which was measured regarding the x-axis, can be inverted, and the following formula (2) so that, with respect to angular-velocity components, components regarding axes other than the x-axis can be inverted. In addition, the rotation matrix R can be provided so as to be in accordance with an coordinate system at the time when the measurement is executed, and more specifically, the rotation matrix R can be provided so as to be in accordance with the directions of the motion measurement devices and the like at the time they are attached to individual parts of human bodies.

$$R_a = \begin{bmatrix} -1 & 0 & 0 \\ 0 & 1 & 0 \\ 0 & 0 & 1 \end{bmatrix} \quad (1)$$

$$R_\Omega = \begin{bmatrix} 1 & 0 & 0 \\ 0 & -1 & 0 \\ 0 & 0 & -1 \end{bmatrix} \quad (2)$$

Therefore, in the case of a condition shown in FIG. 4, a right-and-left transformation matrix for transforming a set of prescribed motion data regarding a right wrist (a set of right-hand data) into a set of prescribed motion data regarding a left wrist (a set of left-hand data) results in the following formula (3).

$$R_a = \begin{bmatrix} R_a & 0 \\ 0 & R_\Omega \end{bmatrix} \quad (3)$$

The feature extraction unit 24 is configured to extract features of an acquired set of prescribed-motion data for each part of the human body of the exemplar person A and features of an acquired set of prescribed-motion data for each part of the human body of the examinee B from the sets of prescribed-motion data Aa to Ae regarding the exempla A and the sets of prescribed-motion data Ba to Be regarding the examinee B, which are acquired by the prescribed motion data acquisition unit 21.

Here, a feature extraction method will be described below. The feature extraction unit 24 is configured to, when exemplar features and examinee features are extracted from each of sets of prescribed-motion data (sets of acceleration data and sets of angular-velocity data), sequentially apply, for example, a sliding window having a constant duration (i.e., a time window having a constant duration) to the stream of time series data within each of the detection intervals resulting from segmentation of a set of prescribed motion-data, and calculate an average feature vector and a standard deviation vector regarding the stream of time series data falling within the sliding window. Further, for each of the detection intervals, average values are calculated with respect to average feature vectors and standard deviation vectors for respective windows included in the detection interval, and thereby, an average vector $\mu$ (a six-dimensional vector) and an deviation vector $\sigma$ (a six-dimensional vector), that is, a feature vector (a twelve-dimensional vector) can be obtained. In the case where the number of the detection intervals resulting from segmentation of the prescribed postures/motions is n, the extraction of the average vector $\mu$ and the deviation vector $\sigma$ for each of the detection intervals resulting from segmentation of the prescribed motions enables extraction of exemplar features (an exemplar-feature-vector) of $12n$ dimensions regarding a set of prescribed motions which is measured by the motion measurement device 10a. Further, in the same manner as or a manner similar to that of the above-described case, from each of the sets of prescribed-motion data Ab to Ae which are measured by the other motion measurement devices 10b to 10e attached to the human body of the exemplar A, exemplar features (an exemplar-person-feature vector) can be extracted. Furthermore, examinee features (an examinee-feature-vector) is extracted from each of the sets of prescribed-motions Ba to Be which are measured by the motion measurement devices 10b to 10e attached to the human body of the examinee B. In addition, with respect to methods of extracting such features, it is possible to utilize technologies described in the non-patent literature: Ling Bao, Stephen S. Intille, "Activity Recognition from User-Annotated Acceleration Data", In Second International Conference on Pervasive Computing, pp. 1-17, 2004, and the like.

The transformation matrix calculation unit 25 is configured to, for each of the parts of the human body, calculate a transformation matrix for performing a data transformation between features of a set of prescribed-motion data regarding the exemplar A and features of a set of prescribed-motion data regarding the examinee B.

Here, a method of calculating the above-described transformation matrix will be described below. Assuming that feature vectors (twelve-dimensional vectors) for each of the detection intervals, which are extracted from a set of prescribed-motion data $A_p$ resulting from measurement at a part P of the human body of the exemplar A and a set of prescribed-motion data $B_p$ resulting from measurement at a part P', which corresponds to the position P, of the human body of the examinee B, are denoted by $\mu^A_p$ and $\mu^B_p$, respectively, the relationship therebetween can be represented by a formula (4) as an affine transformation. Therefore, from the formula (4), it is possible to calculate a transformation matrix T which performs an affine transformation from a feature vector regarding the exemplar A to a feature vector regarding the examinee B for each of the detection intervals. In this embodiment, an average of the transformation matrixes Ts resulting from calculation for respective detection intervals is calculated, and this calculated average is used as a transformation matrix $T_p$ for performing an affine transformation from the features regarding the exemplar A to the features regarding the examinee B.

$$\mu^A_p = A_p \mu^B_p + b_p = T \xi_p \quad (4)$$

In addition, $\xi_p = [1, \mu^B_p]'$ is an average vector, $T = [b_p, A_p]'$ is a transformation matrix, $A_p$ is a 12×12 matrix, and $b_p$ is a vector of 12 dimensions.

The specified-motion data acquisition unit 26 is configured to acquire sets of specified motion data regarding specified motions performed by the exemplar A. That is, the specified-motion data acquisition unit 26 is configured to receive and acquire respective sets of specified motion data Aa to Ae measured by the corresponding motion measurement devices 10a to 10e, which are attached to individual parts of the human body of the exemplar A. The specified-motion data acquisition unit 26 is also configured to acquire pieces of specified motion data Ba to Be regarding specified-motions performed by the examinee B, which are motions the same as those performed by the exemplar A. With respect to the sets of specified-motion data having been acquired in such a manner as described above, the feature extraction unit 24 is configured to, for each of the parts, extract features regarding the specified motions performed by the exemplar A and features regarding the specified motions performed by the examinee B from the set of specified-motion data regarding the exemplar A and the set of specified-motion data regarding the examinee B, respectively. In addition, in order to prevent discrepancies in the positions of the motion measurement devices between two cases, one being a case where the measurement of the prescribed-motion data is performed, the other one being a case where the measurement of the specified-motion data is performed, subsequent to measurement of a set of prescribed-motion data regarding the prescribed motions performed by the exemplar A (or the examinee B), under the condition where the motion measurement devices 10a to 10e remain to be attached to the body of the exemplar A (or the examinee B), it is possible to perform a measurement of a set of specified-motion data regarding the specified motions performed by the exemplar A (or the examinee B).

The creation unit 27 is configured to create a piece of exemplary specified-motion information for examinees from the set of specified-motion data regarding the exemplar A by using the transformation matrix $T_p$. More specifically, the exemplary specified-motion information for examinees is obtained by transforming first features using the transformation matrix $T_p$, the first exemplar features being extracted from a set of specified-motion data regarding the exemplar A, and extracting one or more components from among the components of second features resulting from the transformation. That is, the creation unit 27 is configured to calculate two kinds of vectors, one being a time series of average vectors: $V^A(t) = (g_x(t), g_y(t), g_z(t), a_x(t), a_y(t), a_z(t))$, which is obtained from a set of specified motion data measured at a part p, regarding specified motions performed by the exemplar A, the other one being a time series of deviation vectors: $S^A(t) = (\sigma_{gx}(t), \sigma_{gy}(t), \sigma_{gz}(t), \sigma_{ax}(t), \sigma_{ay}(t), \sigma_{az}(t))'$, which is obtained from a stream of prescribed-motion data falling within a time window resulting from application of a sliding window, and then, create the features as a vector $\mu^A(t)$ ($V^A(t)$ $S^A(t))'$. The features $\mu^A(t)$ is multiplied by a pseudo inverse matrix $T_p^+$ of the transformation matrix $T_p$, that is, the features $\mu^A(t)$, which is obtained from the set of specified-motion data regarding the exemplar A, is transformed by using a formula: $\mu^{A \to B}(t) = T_p^+ \mu^A(t)$, and one or more components of the components of the transformed features are extracted as those of a piece of exemplary specified-motion information for examinees. In addition, assuming that $T_p$ is an M×N matrix, in the case where rank $T_p = M$, the pseudo inverse matrix $T_p^+$ can be uniquely obtained by using a formula: $T_p^+ = T_p'(T_p T_p')^{-1}$, and in the case where rank $T_p = N$, the pseudo inverse matrix $T_p^+$ can be uniquely obtained by using a formula: $T_p^+ = (T_p T_p')^{-1} T_p'$. Therefore, in the case where $T_p$ is not regular but does not have an inverse matrix, an arithmetical operation can be performed. With respect to the sets of motion data regarding parts other than the part p, in the same manner as described above, the corresponding pieces of exemplary specified-motion information for examinees are created from features which are obtained from sets of specified-motion data regarding the exemplar A by using the transformation matrix $T_p$. In addition, each of the transformed features can be obtained by using a formula: $\mu^{A \to B}(t) = (V^{A \to B}(t), S^{A \to B}(t))'$.

Figure 5:
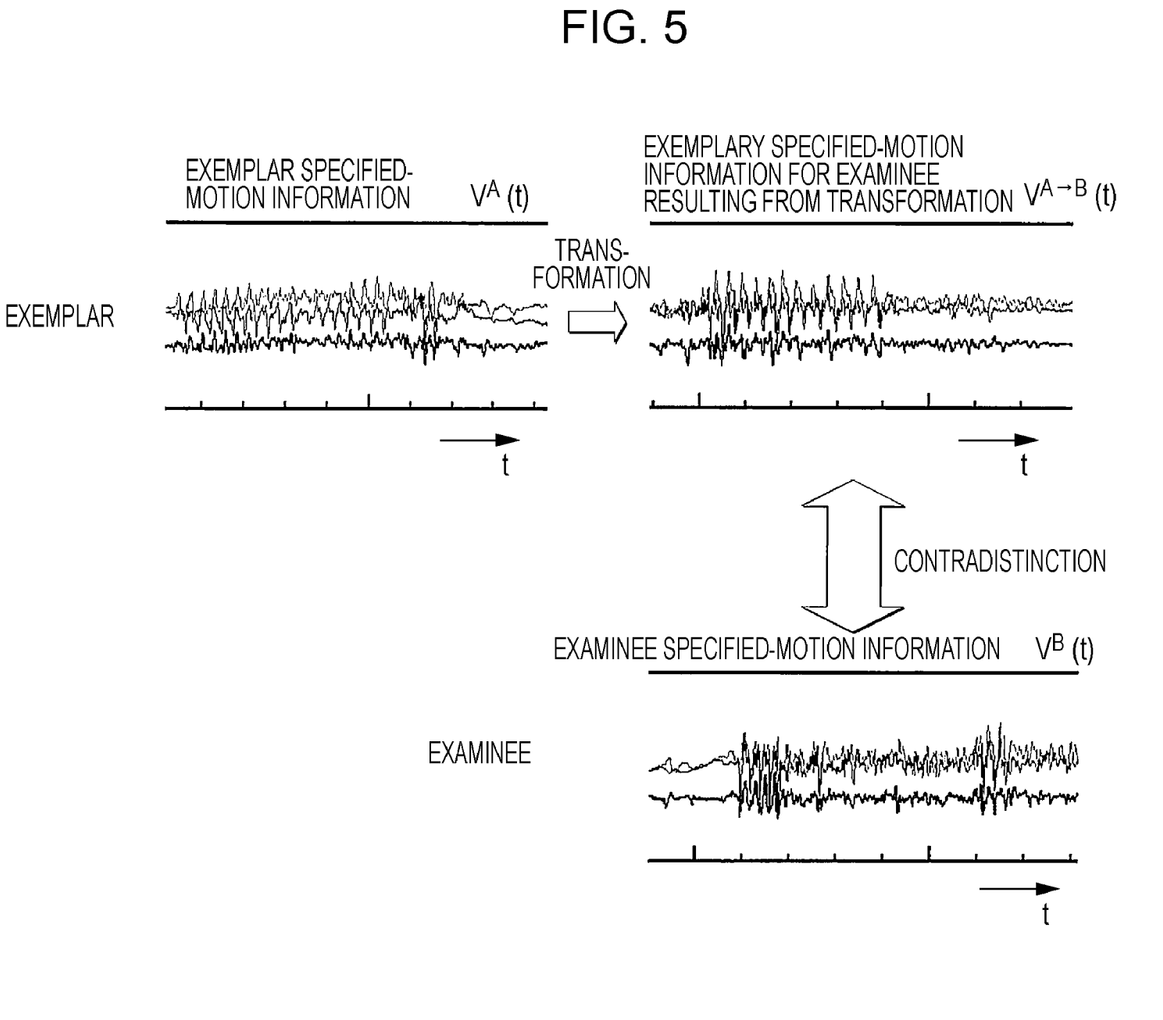
FIG. 5 is a diagram illustrating an example of the demonstration of displaying pieces of specified-motion data regarding an exemplar and an examinee, according to an embodiment of the present disclosure.

The indication unit (presentation unit) 28 is configured to present a piece of actual specified-motion data regarding the examinee B and a piece of exemplary specified-motion information for examinees, which was created by the creation unit 27. The indication unit 28 is configured to, for example, as shown in FIG. 5, display a piece of exemplary specified-motion information for examinees, that is, one or more components (for example, each of acceleration components in an x-axis direction, a y-axis direction and a z-axis direction) included in the transformed features $V^{A \to B}(t)$, and components (a piece of examinee specified motion information), being included in the features $V^B(t)$ obtained from an actual set of specified-motion data regarding the examinee B, and corresponding to those of the above-described piece of exemplar specified-motion information for examinees, on a display unit, such as a display of the motion analysis device 20. In FIG. 5, a waveform shown in an upper-left area is an example of a piece of exemplar specified-motion information (an original piece of information, from which a piece of exemplary specified-motion information for examinees is transformed by using the transformation matrix Tp), a waveform shown in an upper-right area is an example of a piece of exemplary specified-motion information for examinees, which is transformed from the piece of exemplar specified-motion information so as to be adapted to the physique of the examinee B, and a waveform shown in a lower-right area is an example of a piece of examinee specified-motion information. In addition, with respect to each of the waveforms, a horizontal axis denotes a time (t), and a vertical axis denotes an acceleration (G). Here, among components included in the transformed piece of exemplar features: $\mu^{A \to B}(t)=(V^{A \to B}(t), S^{A \to B}(t))'$, one or more components included in $V^{A \to B}(t)$ can be displayed for examinees and the like. In addition, when displaying is performed for examinees and the like, $S^{A \to B}(t)$ can be displayed as a piece of information indicating a fluctuation band regarding $V^{A \to B}(t)$.

Figure 6:
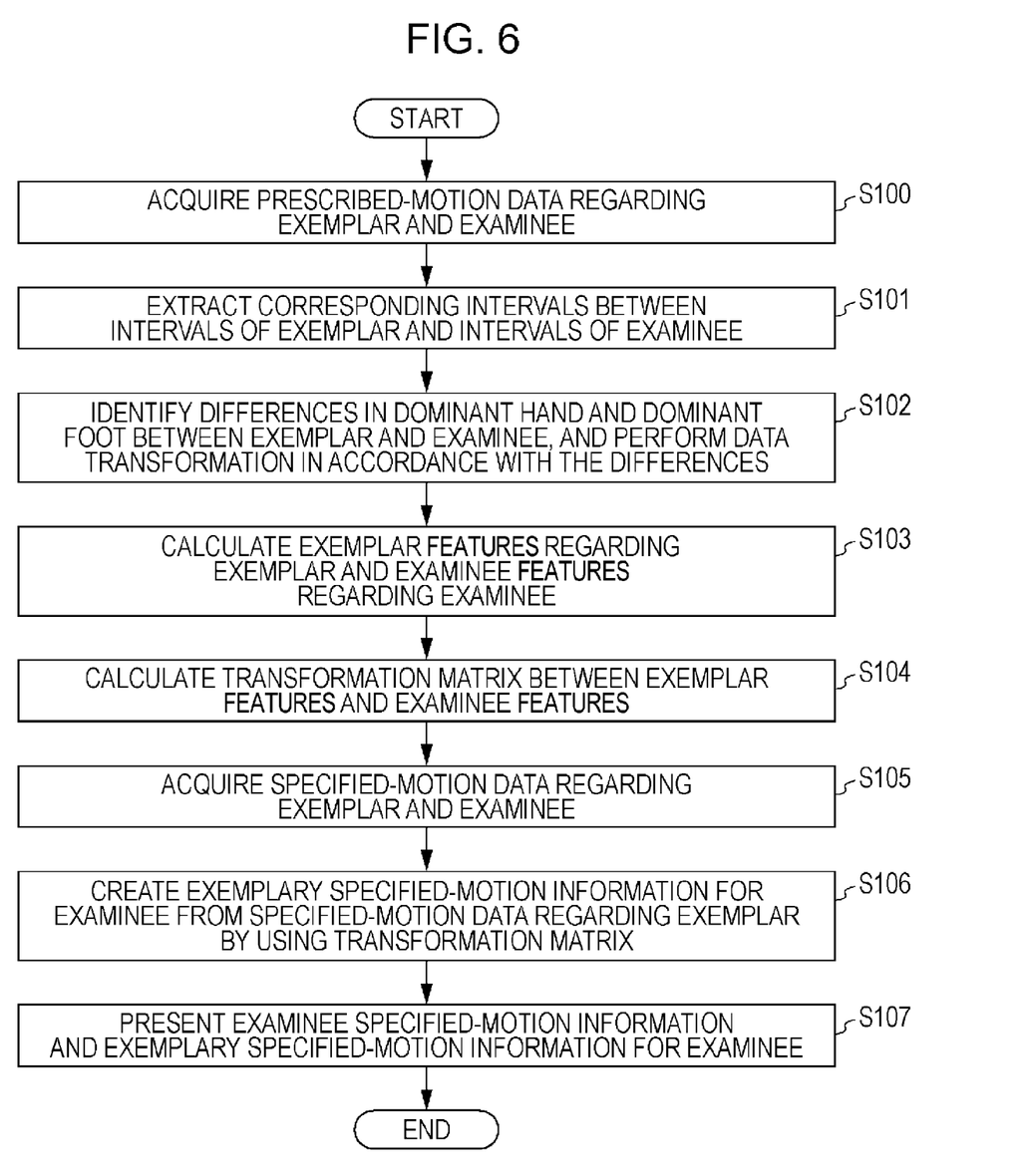
FIG. 6 is a diagram illustrating an example of a flowchart of processes of a motion analysis, performed by a motion analysis device according to an embodiment of the present disclosure.

Hereinafter, a method of a motion analysis according to this embodiment, which is performed by using the motion analysis device 20, will be described with reference to a flowchart shown in FIG. 6. The flowchart shown in FIG. 6 includes two processing stages, one being a transformation matrix calculation stage, in which sets of prescribed-motion data regarding the exemplar A and the examinee B are measured and a transformation matrix is calculated, the other one being a indication stage, in which, subsequent to the calculation of the transformation matrix, an actual set of specified-motion data regarding the exemplar A is transformed into a piece of exemplary specified-motion information for examinees and the piece of specified-motion information for examinees resulting from the transformation is presented. Further, the flowchart will be described by way of an example in which the above-described "deep breath" including nine prescribed postures/motions is provided as a series of prescribed motions. In addition, processes included in the flowchart shown in FIG. 6 can be executed in orders each resulting from changing the original order of the processes appropriately, or certain processes of the processes included in the flowchart can be executed in parallel with one another, provided that no inconsistency exists in the context the rearranged processes.

In the transformation matrix calculation stage, firstly, the motion analysis device 20 acquires respective sets of pre-scribed-motion data in the case where the exemplar A performs prescribed motions and in the case where the examinee B performs prescribed motions (in step S100). That is, the motion analysis device 20 receives and acquires sets of prescribed-motion data Aa to Ae which are measured by using the corresponding motion measurement devices 10a to 10e attached to individual parts of the human body of the exemplar A, and further, in the case of the examinee B, in the same manner as described above, the motion analysis device 20 receives and acquires sets of prescribed-motion data Ba to Be which are measured by using the corresponding motion measurement devices 10a to 10e. Further, the motion analysis device 20 performs labeling of a piece of motion identification information (a motion label) on each of the sets of prescribed-motion data Aa to Ae, the sets of prescribed-motion data Aa to Ae being measured by the corresponding measurement devices 10a to 10b attached to the human body of the exemplar A, and then, stores the resultant sets of motion data in the database 29. In the same manner as described above, the sets of prescribed-motion data Ba to Be regarding the examinee B are processed, and the resultant sets of prescribed-motion data are stored in the database 29.

Subsequently, by using the sets of prescribed-motion data Aa to Ae regarding the exemplar A and the sets of prescribed-motion data regarding the examinee B, the motion analysis device 20 extracts the corresponding intervals between the intervals of the sets of prescribed motion data Aa to Ae regarding the exemplar A and the intervals of the sets of prescribed data regarding the examinee B by using a method of detecting the degree of similarity between two streams of time series data, such as the DP matching method (in step S101). For example, when extracting the corresponding intervals between those of a set of prescribed-motion data Aa measured by the motion measurement device 10a, which is attached to the right wrist of the exemplar A, and a set of prescribed-motion data Ba measured by the motion measurement device 10a, which is attached to the right wrist of the examinee B, the motion analysis device 20 detects the degree of similarity between the set of prescribed-motion data Aa and the set of prescribed-motion data Ba, and thereby, extracts an interval Ia, in which the posture of "attention" is made by the exemplar A, and an interval Ib corresponding to the interval Ia, in which the posture of "attention" is made by the examinee B.

Subsequently, in the case where at least any of a difference between a dominant hand of the exemplar A and a dominant hand of the examinee B and a difference between a dominant foot of the exemplar A and a dominant foot of the examinee B arises, the motion analysis device 20 performs a data transformation so as to cause respective sets of prescribed-motion data regarding the corresponding parts (hands and/or foots) of the exemplar person A and the examinee B to correspond to each other (in step S102). For example, assuming that a piece of information regarding dominant hands and dominant foots of the exemplar A and the examinee B is inputted to the motion analysis device 20 in advance, in the case where the exemplar A is a right-handed person and the examinee B is a left-handed person, a set of prescribed-motion data regarding the right wrist of the exemplar A (a set of right-hand data), which is measured by the motion measurement device 10a attached to the right wrist of the exemplar A, is transformed into a set of prescribed-motion data regarding the left wrist of the exemplar A (a set of left-hand data).

Subsequently, the motion analysis device 20 extracts features of an acquired set of prescribed-motion data for each part of the human body of the exemplar person A and features of an acquired set of prescribed-motion data for each part of the human body of the examinee B from the sets of prescribed-motion data Aa to Ae regarding the exempla A and the sets of prescribed-motion data Ba to Be regarding the examinee B (in step S103). As a result of the extraction described above, exemplar features and an examinee features, each being a 12×9 dimension vector, can be obtained for each part of the human bodies of the exemplar A and the examinee B, respectively.

Subsequently, the motion analysis device 20 calculates a transformation matrix between features obtained from a set of prescribed motion-data regarding the exemplar A and features obtained from a set of prescribed motion data regarding the examinee B for each of the parts of the human body (in step S104). By using the above-described method of calculating a transformation matrix, a transformation matrix $T_p$ between features, which is obtained from a set of prescribed motion-data regarding the exemplar A, and features, which is obtained from a set of prescribed motion data regarding the examinee B, can be calculated.

Subsequently, in an indication stage, firstly, the motion analysis device 20 acquires sets of specified-motion data Aa to Ae regarding specified motions performed by the exemplar A (in step S105). That is, the motion analysis device 20 receives and acquires a set of specified-motion data $\mu^A(t)$ having been measured by the corresponding motion measurement device among the motion measurement devices 10a to 10b, which are attached to the corresponding parts of the human body of the exemplar A. In the same manner as described above, the motion analysis device 20 acquires a set of specified-motion data $\mu^B(t)$ regarding specified motions performed by the examinee B, which are the same as those performed by the exemplar A.

Subsequently, by using the transformation matrix $T_p$, the motion analysis device 20 creates a piece of exemplary specified-motion information for examinees from the set of specified-motion data regarding the exemplar A (in step S106). For example, assuming that a formula: $\mu^{A \to B}(t)=T_p^+\mu A(t)$ is satisfied, features $\mu^A(t)$ obtained from a set of prescribed-motion data regarding the exemplar A is transformed into $\mu^{A \to B}(t)$ by using the transformation matrix $T_p$, and one or more components among those of the features resulting from the above-described transformation are extracted as a piece of exemplary specified-motion information for examinees.

Subsequently, the motion analysis device 20 presents a piece of specified-motion information regarding the examinee B and a set of exemplar specified-motion information for examinees, which was transformed by the creation unit 27 (in step S107). For example, as shown in FIG. 5, on the display unit of the motion analysis device 20, the motion analysis device 20 displays a piece of exemplar specified-motion information for examinees, that is, one or more components of those of features $V^{A \to B}(t)$ resulting from transformation performed by the creation unit 27, and an actual piece of an examinee specified-motion information, that is, one or more components of those of features $V^B(t)$ resulting from calculation of a set of specified-motion data regarding the examinee B, the one or more components of those of features $V^B(t)$ and the one or more components of those of the exemplar features $V^{A \to B}(t)$ corresponding to each other.

As described above, according to the motion analysis device and the motion analysis method according to this embodiment, by measuring sets of prescribed-motion data regarding an exemplar and an examinee in advance, calculating transformation matrixes therebetween, and transforming either sets of specified-motion data for the exemplar or sets of specified-motion data for the examinee by using the transformation matrix regarding the specified-motion, it is possible to eliminate differences, such as physique differences due to gender and age, individual differences in a dominant hand, a dominant foot and the like, and discrepancies between the attachment positions of sensors, and make contradistinction between the sets of specified-motion data for the exemplar and those of the examinee. As a result, it is possible to quantitatively present differences in timings, fluctuation bands and postures regarding individual parts of the body of a human being between the specified-motions performed by the exemplar and the examinee, and give the examinee appropriate advices on how to make individual parts of his or her human body to behave.

Further, the motion analysis device and the motion analysis method according to this embodiment can be applied to cases where the degrees of skills of an exemplar and an examinee are likely to be appeared in motions performed thereby. More specifically, the motion analysis device and the motion analysis method according to this embodiment can be applied to great majority of fields, in each of which a piece of specified-motion data regarding an exemplar is extracted, and further, is indicated to beginners for instruction, such as a field in which instructing beginners on a certain motion is necessary for their proficiency, and a field in which the inheritance of a skill of a skilled person (an exemplar) is necessary, with respect to, for example, a great majority of skills for driving or handling a car, an airplane, a ship and the like, and techniques in most portions of sports, in playing musical instruments, in cooking food (i.e., handling a cooking knife, a pan and the like), in medical treatments, nursing cares and elderly cares, and the like.

Hereinbefore, a preferred embodiment of the present disclosure has been described; however, the present disclosure is not limited to the above-described embodiment, but various modifications, addition and deletions can be performed without departing from the philosophy and the scope of the claims of the present disclosure.

For example, in the above-described embodiment, an example, in which a motion measurement device including both an acceleration sensor and a gyro sensor is used, was described; however, the present disclosure is not limited to this example, but, for example, either the acceleration sensor or the gyro sensor may be included therein.

Further, in the above-described embodiment, an example, in which the corresponding interval extraction unit 22 is included and the corresponding segmented intervals are specified thereby, was described; however, this disclosure is not limited to this example, but the corresponding interval extraction unit 22 can be omitted. In this case, for example, by measuring a set of prescribed-motion data regarding the exemplar A in advance, predetermining the corresponding intervals regarding the set of prescribed-motion data, and causing the motion analysis device 20 to perform an indication to the examinee B so that the examinee B can make or perform appropriate postures or motions to be made or performed during each of the corresponding intervals, it is possible to cause intervals common to the sets of prescribed-motion regarding the exemplar A and the sets of prescribed-motion regarding the examinee B to correspond to each other.

Further, in the above-described embodiment, an example, in which dominant hands and dominant foots of an exemplar and an examinee are taken into consideration, was described; however, this disclosure is not limited to this example, but, in accordance with a kind of specified-motion data, taking into consideration of the fact that sets of specified-motion data regarding a dominant hand and a dominant foot are bilaterally symmetric, and the like, can be omitted.

Further, in the above-described embodiment, an example, in which there is only one transformation matrix between an exemplar and an examinee, was described; however, this disclosure is not limited to this example, but, for example, respective transformation matrixes between the exemplar and a plurality of examinees can be calculated and stored in the database 29.

Further, in the above-described embodiment, an example, in which a set of specified-motion data regarding an examinee is measured, as well as a set of specified-motion data regarding an exemplar, was described, however, this disclosure is not limited to this example, but, for example, only the set of specified motion data regarding the exemplar can be measured. In this case, by presenting a piece of exemplary specified-motion information for examinees, it is possible for an examinee to take into consideration differences in a physique and the like between the exemplar and the examinee, and understand how to behave in advance.

Further, in the above-described embodiment, an example, in which transformation matrixes for calculating a set of prescribed-motion data regarding the examinee B from a set of prescribed-motion data regarding the exemplar A are calculated, was described; however, this disclosure is not limited to this example, but, for example, transformation matrixes for calculating a set of prescribed-motion data regarding the exemplar A from a set of prescribed-motion data regarding the examinee B can be calculated. In this case, the pseudo inverse-matrix transformation performed in the above-described embodiment is unnecessary.

Further, in the above-described embodiment, an example, in which the motion analysis device 20 is configured to include units each having processing functions allocated thereto; however, this disclosure is not limited to this example, but, a part of or the whole of the processing functions included in each of the units may be distributed and included in other devices over a network which are communicatably connected to the motion analysis device 20.

Further, in the motion analysis device 20, units each having processing functions specific thereto are included, but certain units selected from among the units included in the motion analysis device 20 may be configured to be integrated into one unit, and further, a certain unit selected from among the units included in the motion analysis device 20 may be separated into a plurality of units.

What is claimed is:

1. An operations analysis apparatus for motion, comprising:
   a prescribed-motion data acquisition unit configured to acquire prescribed-motion data which is measured when an exemplar performs prescribed motions including a series of prescribed postures and motions, by using at least one motion measurement device which is attached to at least one part of the human body of the exemplar, and acquire prescribed-motion data which is measured when an examinee performs the prescribed motions, by using at least one motion measurement device which is attached to at least one part of the human body of the examinee, which corresponds to the at least one part of the human body of the exemplar;
   a corresponding interval extraction unit configured to extract the corresponding intervals between intervals of the prescribed-motion data for the exemplar and intervals of the prescribed-motion data for the examinee, from the prescribed-motion data for the exemplar and the prescribed-motion data for examinee;
   a feature extraction unit configured to, from the acquired prescribed-motion data, extract features of the acquired prescribed-motion data for the exemplar and features of the acquired prescribed-motion data for the examinee, for parts of the human body;
   a transformation matrix calculation unit configured to, on the basis of information for the corresponding intervals extracted thereby, calculate a transformation matrix for performing a transformation between the features of the prescribed-motion data for the exemplar and the features of the prescribed-motion data for the examinee, for the parts of the human body;
   a specified-motion data acquisition unit configured to acquire specified-motion data which is measured when the exemplar and the examinee perform specified motions, respectively, by using the at least one motion measurement device which is attached to the at least one part of the human body of the exemplar and the at least one motion measurement device which is attached to the at least one part of the human body of the examinee;
   a creation unit configured to, from the acquired specified-motion data for the exemplar, create exemplary specified-motion information for the examinee by using the transformation matrix; and
   an indication unit configured to indicate examinee specified-motion information based on the acquired specified-motion data for the examinee, and the created exemplary specified-motion information for the examinee so as to be associated with each other,
   wherein the prescribed-motion data acquisition unit is configured to acquire prescribed-motion data which is measured, by using at least one motion measurement device which is attached to at least one of a dominant hand and a dominant foot of the exemplar, and by using at least one motion measurement device which is attached to at least one of a dominant hand and a dominant foot of the examinee,
   wherein the operations analysis apparatus for motion further comprises a data transformation unit configured to, in the case where the exemplar is a right-handed person and the examinee is a left-handed person, or the exemplar is a left-handed person and the examinee is a right-handed person, perform a data transformation so that the prescribed-motion data for the at least one of a dominant hand and a dominant foot of the exemplar corresponds to the prescribed-motion data for the at least one of a dominant hand and a dominant foot of the examinee, and
   wherein the feature extraction unit is further configured to prevent discrepancies in the positions of the motion measurement devices between acquisition of the prescribed motion data and the specified motion data by measuring a set of specified motion data.

2. An operations analysis apparatus for motion, comprising:
   a prescribed-motion data acquisition unit configured to acquire prescribed-motion data which is measured when an exemplar and an examinee perform prescribed motions including a series of prescribed postures and motions, respectively;
   a feature extraction unit configured to, from the acquired prescribed-motion data, extract features of the prescribed-motion data for the exemplar and features of the prescribed-motion data for the examinee;
   a transformation matrix calculation unit configured to calculate a transformation matrix for performing a transformation between the features of the prescribed-motion data for the exemplar and the features of the prescribed-motion data for the examinee;
   a specified-motion data acquisition unit configured to acquire specified-motion data which is measured when the exemplar performs specified motions, and specified-motion data which is measured when the examinee performs the specified motions;
   a creation unit configured to, from the specified-motion data for the exemplar, create exemplary specified-motion information for the examinee by using the transformation matrix; and
   an indication unit configured to indicate examinee specified-motion information based on the specified-motion data for the examinee, and the exemplary specified-motion information for the examinee so as to be associated with each other, and
   wherein the feature extraction unit is further configured to prevent discrepancies in the positions of the motion measurement devices between acquisition of the prescribed motion data and the specified motion data by measuring a set of specified motion data.

3. The operations analysis apparatus for motion according to claim 2,
   wherein the prescribed-motion data acquisition unit is further configured to acquire prescribed-motion data measured by at least one motion measurement device which is attached to at least one part of the body of the exemplar, and prescribed-motion data measured by at least one motion measurement device which is attached to at least one part of the human body of the examinee,
   wherein the feature extraction unit is further configured to extract the features for the exemplar and the features for the examinee, for parts of the human body, and
   wherein the transformation matrix calculation unit is further configured to calculate a transformation matrix for performing a transformation between the features for the exemplar and the features for the examinee, for the parts of the human body.

4. The operations analysis apparatus for motion according to claim 2, further comprising a corresponding interval extraction unit configured to extract the corresponding intervals between the intervals of the prescribed-motion data for the exemplar and the intervals of the prescribed-motion data for the examinee, from the prescribed-motion data for the exemplar and the prescribed-motion data for examinee, wherein the transformation matrix calculation unit is configured to, on the basis of a piece of information for the corresponding intervals extracted thereby, calculate a transformation matrix for performing a transformation between the features for the exemplar and the features for the examinee.

5. The operations analysis apparatus for motion according to claim 2, wherein the prescribed-motion data acquisition unit is further configured to acquire prescribed-motion data which is measured, by using at least one motion measurement device which is attached to at least one of a dominant hand and a dominant foot of the exemplar, and by using at least one motion measurement device which is attached to at least one of a dominant hand and a dominant foot of the examinee, and wherein the operations analysis apparatus for motion further comprises a data transformation unit configured to, in the case where the exemplar is a right-handed person and the examinee is a left-handed person, or the exemplar is a left-handed person and the examinee is a right-handed person, perform a data transformation so that the prescribed-motion data for the at least one of a dominant hand and a dominant foot of the exemplar corresponds to the prescribed-motion data for the at least one of a dominant hand and a dominant foot of the examinee.

6. The operations analysis apparatus for motion according to claim 2, wherein each of the exemplar features and the examinee features includes at least one of an acceleration component and an angular-velocity component.

7. A motion analysis method for motion, performed by a computer device having a database, the method comprising the steps of:

causing a prescribed-motion data acquisition unit which is realized by the computer device executing a program, to acquire prescribed-motion data for an exemplar and an examinee, respectively, in the case where the exemplar and the examinee perform prescribed motions including a series of prescribed postures and motions, and to store the acquired prescribed-motion data in the database;

causing a feature extraction unit which is realized by the computer device executing a program, to extract features of the prescribed-motion data for the exemplar and features of the prescribed-motion data for the examinee, from each set of the prescribed-motion data stored in the database;

causing a transformation matrix calculation unit which is realized by the computer device executing a program, to calculate a transformation matrix for performing a transformation between the exemplar features and the examinee features;

causing a specified-motion data acquisition unit which is realized by the computer device executing a program, to acquire specified-motion data which is measured when the exemplar performs specified motions, and specified-motion data which is measured when the examinee performs the specified motions, and to store the acquired specified-motion data in the database;

causing the feature extraction unit to prevent discrepancies in the positions of the motion measurement devices between acquisition of the prescribed motion data and the specified motion data by measuring a set of specified motion data;

causing a creation unit which is realized by the computer device executing a program, to create exemplary specified-motion information for the examinee from the specified-motion data for the exemplar stored in the database, by using the calculated transformation matrix; and causing an indication unit which is realized by the computer device executing a program, to indicate examinee specified-motion information based on the specified-motion data for the examinee, and the exemplary specified-motion information for the examinee so as to be associated with each other.

* * * * *

UNITED STATES PATENT AND TRADEMARK OFFICE
CERTIFICATE OF CORRECTION

| | | |
|---|---|---|
| PATENT NO. | : 8,113,843 B2 | Page 1 of 1 |
| APPLICATION NO. | : 12/642265 | |
| DATED | : February 14, 2012 | |
| INVENTOR(S) | : Naya | |

It is certified that error appears in the above-identified patent and that said Letters Patent is hereby corrected as shown below:

On the Title Page, in Field (56), under "FOREIGN PATENT DOCUMENTS", in Column 2, Line 4, delete entry "JP 2005-11178  * 4/2005".

In Column 1, Line 27, delete "2004" and insert -- 2004. --, therefor.

In Column 3, Line 49, delete "DESCRIPTION" and insert -- DETAILED DESCRIPTION --, therefor.

In Column 8, Line 38, delete "an deviation" and insert -- a deviation --, therefor.

In Column 10, Lines 14-15, delete "$\mu^A(t)\ (V^A(t)\ S^A(t))'.$" and insert -- $\mu^A(t) = (V^A(t), S^A(t))'.$ --, therefor.

In Column 10, Line 58, delete "Tp)," and insert -- $T_p$), --, therefor.

In Column 12, Line 67, delete "μA (t)" and insert -- $\mu^A(t)$ --, therefor.

Signed and Sealed this
Twenty-sixth Day of June, 2012

David J. Kappos
*Director of the United States Patent and Trademark Office*